United States Patent [19]

Moy

[11] Patent Number: 5,759,555
[45] Date of Patent: Jun. 2, 1998

[54] COSMETIC FORMULATION AND METHOD FOR AMELIORATION OF SKIN KERATOSES AND STRIAE DISTENSAE

[76] Inventor: Lawrence S. Moy. 2219 Gates Ave., #B, Redondo Beach, Calif. 90278

[21] Appl. No.: 660,273

[22] Filed: Jun. 7, 1996

[51] Int. Cl.⁶ .................................................. A61K 7/48
[52] U.S. Cl. ........................................ 424/401; 424/195.1
[58] Field of Search ................................. 424/401, 195.1

[56] References Cited

U.S. PATENT DOCUMENTS

| | | | |
|---|---|---|---|
| 3,864,477 | 2/1975 | Thuillier et al. | 424/94 |
| 3,879,537 | 4/1975 | Van Scott et al. | 424/311 |
| 3,920,835 | 11/1975 | Van Scott et al. | 424/311 |
| 3,984,566 | 10/1976 | Van Scott et al. | 424/283 |
| 3,988,470 | 10/1976 | Van Scott et al. | 424/283 |
| 4,105,783 | 8/1978 | Yu et al. | 424/283 |
| 4,197,316 | 4/1980 | Yu et al. | 424/317 |
| 4,234,599 | 11/1980 | Van Scott et al. | 424/279 |
| 4,246,261 | 1/1981 | Van Scott et al. | 424/240 |
| 4,380,549 | 4/1983 | Van Scott et al. | 424/317 |
| 5,037,803 | 8/1991 | Gueyne et al. | 514/2 |
| 5,153,174 | 10/1992 | Band et al. | 514/12 |

OTHER PUBLICATIONS

Pharmacology of Connective Tissue Effect of Avacado and Soybean Unsaponifi-]Ables on Metabolism of the Intercellular Matrix, A.M. Robert et al., Jan. 10, 1975.

*Primary Examiner*—Jyothsan Venkat
*Attorney, Agent, or Firm*—Price, Gess & Ubell

[57] ABSTRACT

Stretch marks, keratoses and other skin lesions can be ameliorated or cured through repeated topical application, to affected skin, of a dermatological composition containing unsaponifiable lipids extracted from avocado seeds. The effective composition is an emulsion containing between about 5 and 15 weight percent of the unsaponifiable lipids. The effectiveness of the composition is augmented by the addition of zinc and/or copper chelates.

13 Claims, 3 Drawing Sheets

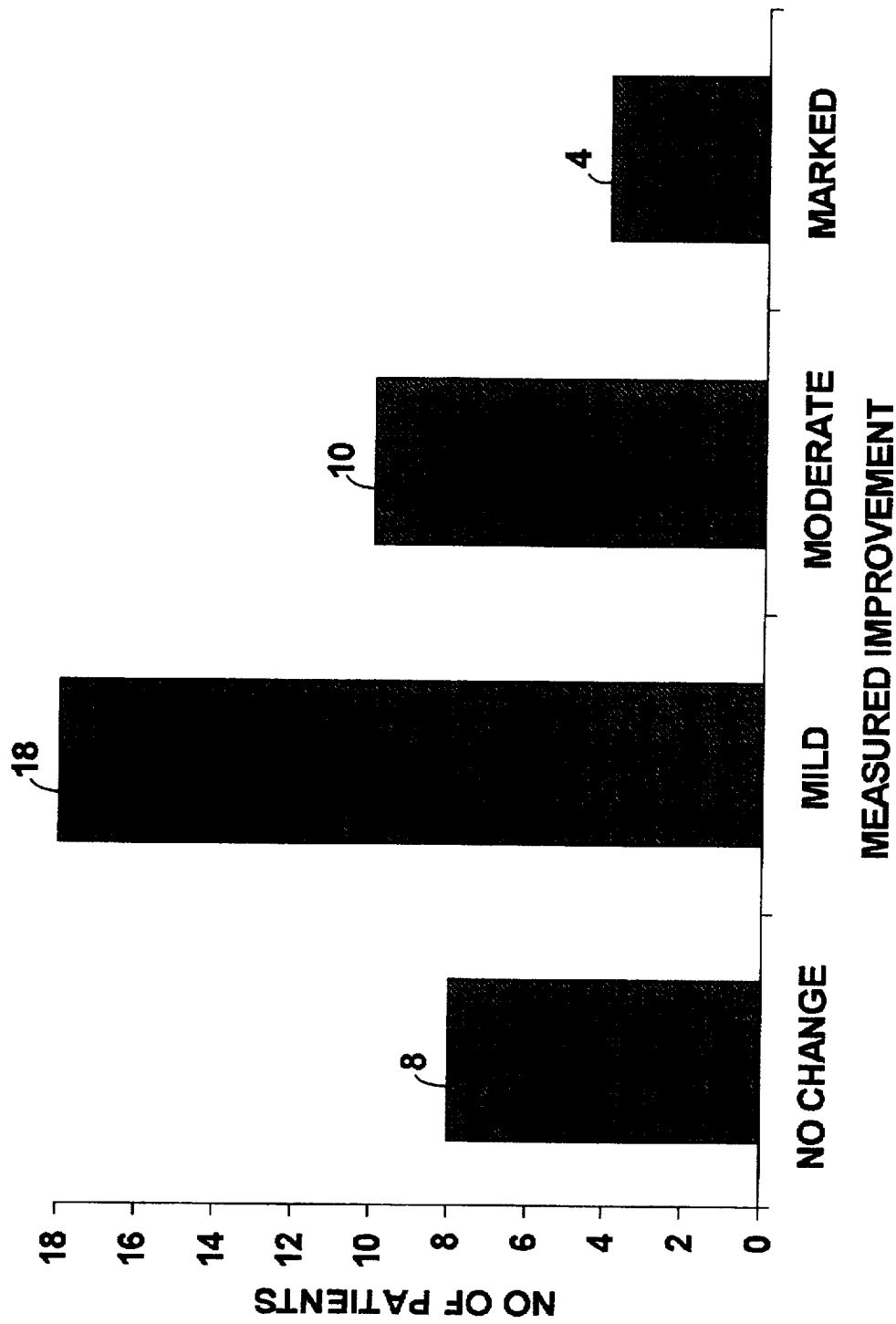

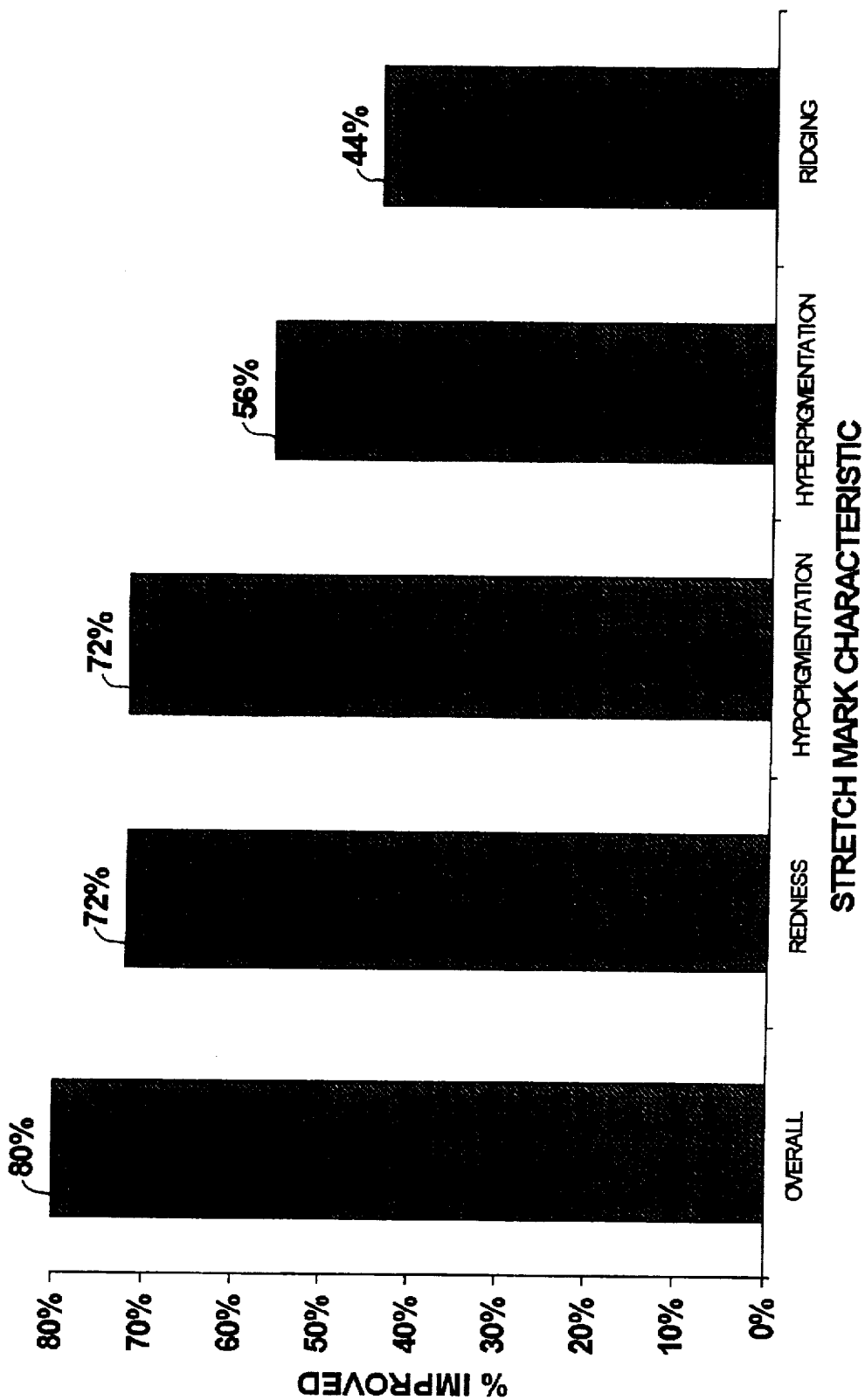

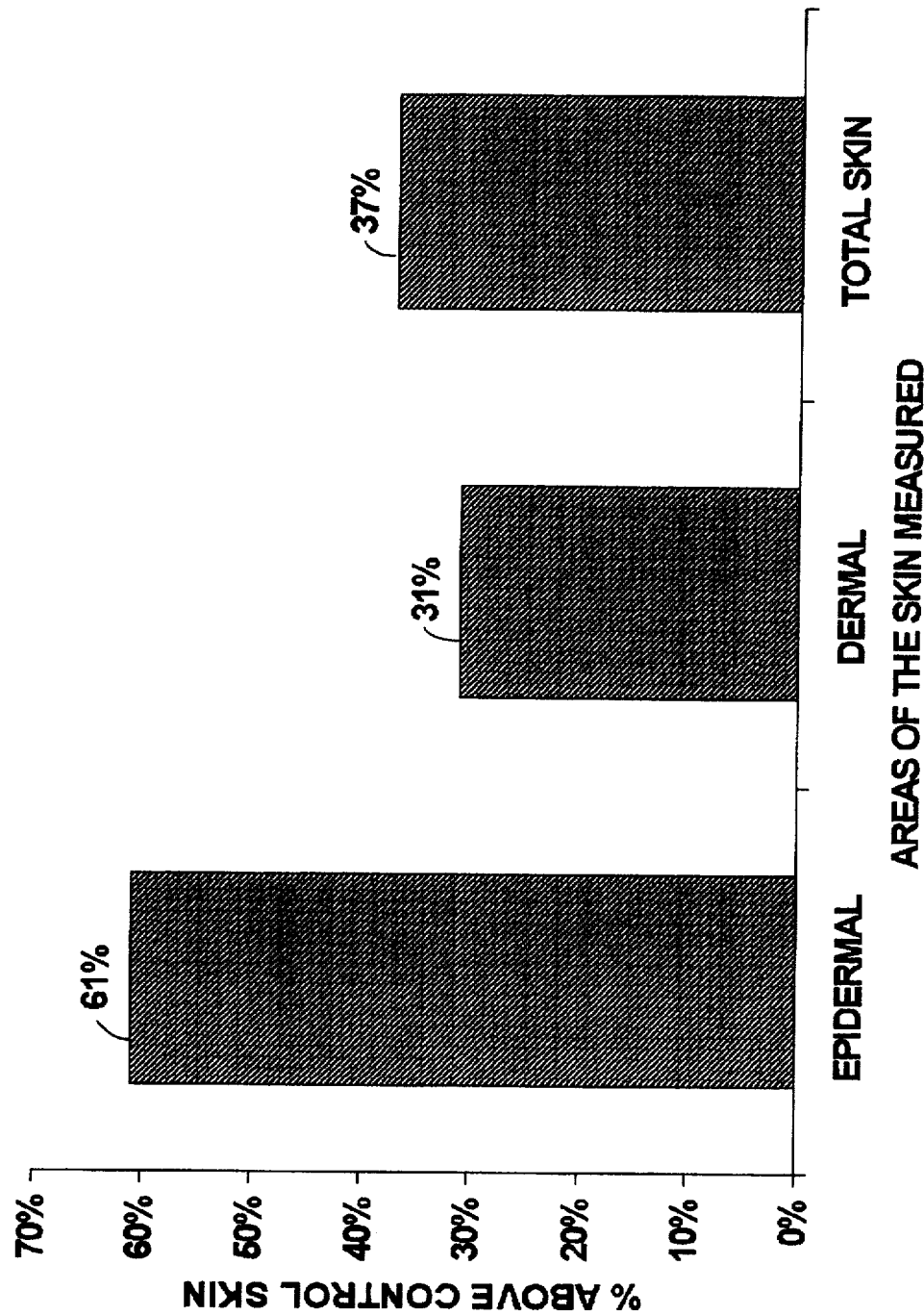

COSMETIC FORMULATION AND METHOD FOR AMELIORATION OF SKIN KERATOSES AND STRIAE DISTENSAE

BACKGROUND OF THE INVENTION

1. Field of the Invention

The present invention deals with the field of cosmetic preparations for improving the appearance of the human skin and, more particularly, with topical formulations for ameliorating skin lesions such as keratoses (rough exfoliating skin due to photodamage, etc.),as well as lesions showing weakened collagen fibers such as striae distensae (stretch marks).

2. Description of Related Art

Keratoses are extremely common skin lesions comprising regions of scaly, exfoliating skin caused either by sun damage (actinic keratoses) or by simple aging of the skin (nonactinic or senile keratoses). These areas of damaged skin can be surgically removed or chemically destroyed. Either of these treatments can be painful and scarring. These lesions yield, to some extent, to various topical applications of various moisturizing cosmetic substances. There has also been some success in treating these lesions with retinoic acid (see U.S. Pat. No. 3,920,835 to Van Scott et al.) and $\alpha$ hydroxy-fatty acids (see U.S. Pat. No. 4,234,599 to Van Scott et al.).

Stretch marks or striae distensae are common blemishes on human skin that usually are even more recalcitrant to treatment than keratoses. Stretch marks are most prevalent on females appearing in the form of white lines or "zebra stripes" and are a rather frequent complication of pregnancy. As the name suggests, the marks are commonly believed to result from the excessive stretching of the skin caused by rapid weight gain, although changes in the levels of various glucocortical hormones have also been implicated.

Normally, the skin is elastic and pliable and can adjust to increases in body girth. However, when the changes are too rapid, the skin's ability to adjust may be overwhelmed. Histologically stretch marks seem to represent a region of skin with absent or disorganized collagen bundles. Although some of the pregnancy-induced marks diminish or even disappear after pregnancy, the more severe marks are usually permanent.

Stretch marks are also formed during the adolescent growth spurt being found on adolescent males as well as females. Significant changes in weight or body size as with body builders can also induce stretch marks. There has been a considerable effort to provide preparations that either prevent the occurrence of the marks and/or promote their healing. Conventional folk wisdom has suggested that applications of various creams or emollients may have the desired effect, but there is considerable clinical controversy surrounding claims that creams and the like can have any significant effect on stretch marks.

A recent study (Madlon-Kay, D. J., *Archives of Family Medicine*, 2:507-11 (1993)) found that application of various creams and oils to the skin of pregnant women had no effect on the formation of stretch marks. However, another recent study (Wierranq, F.; Kozak, W.; Schramm, W.; and Grunberger, W.; *Wiener Klinische Wochenschrift*, 104: 42-44 (1992)) compared a control group of 26 pregnant women with a treatment group of 24 pregnant women who were treated with applications of water/oil massage cream. This study found that whereas two-thirds of the control group developed stretch marks, only one-third of the treatment group did so. It is not clear whether the massage given in applying the preparation influences the apparent beneficial results.

U.S. Pat. No. 5,134,163 to Kingman proposes using topical applications of retinoic acid (tretinoin) to prevent and treat the lesions of striae distensae. A recent article (Elson, M. S., *J. Dermatologic Surgery and Oncology*, 16: 267-70 (1990)) reports improvements in the lesions of 15 of 16 patients treated with a topical tretinoin preparation. So it seems clear that topical application of active compounds can affect stretch marks. However, systemic retinoic acid absorption can result in birth defects and other undesirable side effects such as redness or dryness. Therefore, the material is available only under prescription.

U.S. Pat. No. 4,871,752 to Ilg et al. describes the use of aryloxycarboxylic acid derivatives as a treatment for stretch marks and various other dermatological conditions. These substances, however, are powerful drugs affecting lipid metabolism and seem to give the best results when applied topically together with ultrasound treatments.

U.S. Pat. No. 4,054,649 to Cariel describes the use of a topical solution containing extract of Alchemilla or Alchemilla with Hedera and/or Equisetum to ameliorate a number of dermatological disorders among which are stretch marks. Again, it is apparent from this work that plant extracts, as opposed to synthesized drugs, can also ameliorate stretch marks. However, Alchemilla is neither a commonly available nor commonly used herb in the United States at this time.

Keratoses due to photodamage or age may also show altered cellular constituents including weakened collagen fibers which are not inconsistent with stretch mark lesions. In fact, as mentioned above, there are patents employing retinoic acid to treat stretch marks. There has been considerable research aimed at treating photodamage to skin with retinoic acid.

It has now been discovered that a particular fraction of plant lipids, especially those from avocados or avocado seeds, are unexpectedly efficacious in treating both stretch marks and keratoses.

OBJECTS AND SUMMARY OF THE INVENTION

It is an object of the present invention to add to the small number of topical treatments effective to ameliorate stretch marks and keratoses, such as those dues to photodamage;

It is a further object of the present invention to ameliorate stretch marks and photodamage using naturally occurring compounds thus avoiding a need to employ potentially harmful drugs; and It is also an object of the present invention to provide a treatment for stretch marks that generally improves the characteristics of the surrounding skin while ameliorating stretch marks.

These and other objects are met by a method of ameliorating stretch marks and keratoses, such as those due to photodamage, through repeated topical application, to affected skin, of a dermatological composition containing unsaponifiable lipids extracted from avocado seeds. The effective composition is generally an emulsion of water and oil containing between about 5 and 15 weight percent of the unsaponifiable lipids. The effectiveness of the composition is augmented by the addition of zinc and/or copper chelates.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 shows a graphical representation of a first study on the effect of unsaponifiable avocado lipid-based cosmetics on stretch marks;

FIG. 2 shows results of a third study designed to determine which stretch mark characteristics were improved by application of a unsaponifiable avocado lipid-based cream; and FIG. 3 shows the results of a fifth study which measured effect of application of unsaponifiable avocado lipid-based cosmetic on skin thickness.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a topical composition for the amelioration of stretch marks and keratoses of photodamaged or aged skin containing an effective quantity of an unsaponifiable fraction of a lipid extract of avocado or avocado seeds.

Avocado oils extracted from the seed (pit) of the avocado or, in some cases, actually produced from the lipid rich fruit, have been previously used in cosmetic preparations as have most oils of plant origin. The oil contains mostly glycerides of common plant fatty acids such as palmitic, stearic, oleic, arachidic, and linoleic acids. Further, particularly in the avocado fruit, the same fatty acids are present as phospholipids rather than as glycerides.

The above-mentioned plant lipids are all "saponifiable" in that they can be reacted with an alkali hydroxide such as sodium hydroxide to form a water soluble soap. After the saponifiables are removed, the unsaponifiable organics remain. This fraction of avocado oil has not been well characterized, but appears to contain alkanes, long chain alcohols, triterpenic alcohols, and sterols. The sterol fractions are known to contain stigmasterol, sitosterol, and campesterol.

At least one study (A. M. Roberts et al. *G.M. de France*, 82: (1975)) has been made describing the effects of ingestion (by rats) of the unsaponifiable fractions of avocado seed oil and soybean oil. The avocado oil unsaponifiable fraction was mixed with soybean oil unsaponifiable fraction and compared to stigmasterol. The study showed that ingestion of the unsaponifiable fractions increased the amount of lipid in the skin and also altered the amount of skin collagen. This effect was somewhat similar to that shown by stigmasterol, but the sterol did not increase the skin lipids as greatly as did the avocado-soy unsaponifiable fraction mixture. This implies that the unsaponifiables contain some active ingredient beyond stigmasterol. However, topical cosmetic application of these materials would not be expected to have the effects similar to those produced by ingestion.

Although avocado oil has been reported to possess beneficial cosmetic properties such as increasing skin smoothness, there have hitherto been no indications that unsaponifiable fractions of avocado oil (UFA) have any cosmetic properties beyond those expected from any plant wax or oil. Therefore, the present inventor was surprised to discover that relatively simple cosmetic preparations containing an effective (about 5–15 weight percent) concentration of UFA in a bland dermatologically acceptable vehicle show a dramatic ability to ameliorate skin blemishes such as stretch marks and keratoses. Of course, higher concentrations of UFA than 15 weight percent can be used, but there appears to be little increase in effectiveness and such formulations are more expensive and/or more difficult to compound.

UFA can be prepared by using conventional methods of saponification to remove saponifiable lipids from organic solvent (i.e., hexane) extracts of avocado seeds. Alternatively, lipids can be pressed from the seeds particularly at elevated temperatures or with the aid of steam, as is well known in the art of extracting plant products. The lipids produced by pressing may be somewhat dark in color and may have a more distinct odor. The present inventor has found that well-known preparative column chromatographic methods such as purification overactivated silica gel produce UFA of a light color and essentially no odor. This chromatographically purified product is greatly preferred in the present invention.

First Study

A clinical study was designed to demonstrate the efficacy of UFA-based cosmetics. In particular, the effects on stretch marks were studied because stretch marks are usually considered to be intractable and because stretch marks represent a relatively easy-to-measure skin defect. Female volunteers with stretch marks on their thighs were used in the study. The volunteers had no current illnesses and were not pregnant or undergoing any hormone therapy at the time of the study.

In an initial evaluation the volunteers were instructed to apply cream from one container to one thigh and cream from a second container to the other thigh. UFA-based cream was randomly placed in one container, while the same cosmetic cream, but lacking UFA, was placed in the other container. After six weeks of twice-daily applications, the thighs of the volunteers were evaluated both by experts and by the patients themselves. FIG. 1 shows the overall results of this study. Out of the 40 participants 28 showed mild or moderate improvement, while 4 showed marked improvement. Thus, 32 of the 40 volunteers showed at least some degree of improvement.

Second Study

A second study was undertaken to verify that an expert grader could repeatably detect improvement caused by a UFA-based cream. Twenty patients applied the active cream to one side of their body and the control cream lacking UFA to the other side. After four weeks an expert who was blinded as to which area of the patients' body received the UFA-based cosmetic evaluated the results. In 19 of the 20 cases the side of the body that the expert determined was the most improved had actually received the UFA cosmetic. Thus, use of UFA cosmetic is highly correlated with improvement in the appearance of stretch marks.

Third Study

This study sought to quantitate characteristics of the improvements caused by UFA cosmetic. As in the earlier study, UFA cream was applied against a control cream for six weeks by 40 patients. At the end of this time period the stretch mark lesions were scored for redness and hypopigmentation, hyperpigmentation, ridging, and overall improvement.

The results are shown in FIG. 2. About 80% of the patients showed overall improvement in their stretch marks.

Redness and hypopigmentation, both indications of recent stretch marks, showed a high degree of improvement (72%). One might expect that more recent stretch marks would be more liable to show improvement. However, hyperpigmentation and ridging also showed significant improvement of about 56% and 44%, respectively.

Fourth Study

Attempts were made to measure changes in physical skin properties as a means to understand the underlying mechanism of the UFA-based cosmetic. Again, application of UFA-based cosmetic was compared to application of a control product lacking UFA. The moisturization of skin was measured with a transepidermal water loss measurement device. Skin elasticity was measured by applying controlled pressure to the skin with a probe that also measured the resulting stretching of the skin. These measurements demonstrated that when the UFA-based cream was applied regularly over a two-week period there was a 33% increase in skin moisture retention as compared to the control cream. In addition, there was an 8% increase in skin elasticity with the UFA application. The mechanisms behind these changes are still under investigation, but may be related to histological changes.

Fifth Study

Skin biopsies were obtained from skin treated for six weeks with either the UFA-based cosmetic or with the control cream. The biopsies were sectioned and stained by usual methods. The thickness of the epidermal and dermal layers were then measured.

Results of the skin measurements are displayed in FIG. 3. As compared to the control skin, the skin treated with UFA cosmetic showed about a 37% increase in thickness. The epidermal layer was about 61% thicker than the control, while the dermal layer was about 31% thicker.

Sixth Study

Stretch marks are generally believed to be exceptionally difficult or impossible to treat. The above studies demonstrate the unexpected activity shown by special formulation of unsaponifiable avocado lipids. Other skin lesions, especially those showing some structural similarity to stretch marks, also respond to compositions of the current invention. Because of the dramatic improvement of stretch marks the UFA-based cosmetic was tested on keratoses. Fifteen patients were selected having keratoses on their upper or lower arms. The patient's ages varied between 25 and 65 years, so that many of the keratoses were probably of actinic origin. As in the other studies, the patients were blinded as to the nature of the cosmetic applied. They were instructed to apply cream from one container to their right arm and cream from another container to their left arm, two times daily.

One container contained either 10% UFA in a typical cosmetic base (similar to Formula 1, below). The other container held the same formula with additional corn oil substituted for the UFA. After five weeks the results were evaluated by a clinical expert unaware of which arm received the UFA treatment. About 75% of the patients showed good improvement to complete resolution of the keratoses on the UFA treated arm. The arm receiving the corn oil mixture appeared smoother than before the treatment (anecdotal information from the patients). Two of the patients showed significant improvement to the corn oil-treated arm, as well as the UFA-treated arm. The remaining 25% of the patients showed moderate to little improvement. It is not known whether longer treatment would result in increased improvement or whether the keratoses reappear later.

Formulation

The studies detailed above were performed using an effective quantity of purified UFA (5–10% w/v) in a bland skin cream vehicle. Such formulations are well known in the art. Formulations of the type used in the current invention are often creams of the oil in water emulsion type although formulations with an abundant fatty phase (greater than 50% by weight) are water in oil emulsions. The fatty phase of these creams may comprise as little as about 10% to over 90% by weight of the cream. More typically the creams comprise between 25% and 75% fatty phase by weight.

Besides the UFA, the fatty phase may contain any of a large number of oils, waxes, and fats including fatty acids as well as petroleum oils. Emulsifying agents, generally from about 2% to 10% by weight, may be added to ensure emulsification. Common emulsifying agents are surface active agents such as polysorbate (TWEEN), other polyoyxyethylene-fatty acid or polyglycerol-fatty acid compounds or lanolin soaps, etc. In addition, various thickeners such as silicates (i.e. aluminum or magnesium silicate and various clay minerals and organic modifications thereof) and organic polymers such as cellulose, its derivatives, and vinyl polymers such as CARBOPOL (produced by the B.F. Goodrich company) can be added to improve the consistency of the final product.

Some typical examples are given below but should not be taken as limiting the present invention. Virtually any bland cream formulation, many of which are well known in the art, would be suitable providing it incorporates an effective concentration of UFA.

Example 1

| | |
|---|---|
| UFA | 8.0 |
| oleic acid | 6.0 |
| corn oil | 5.0 |
| Mineral Oil | 4.0 |
| propylene glycol | 3.0 |
| TWEEN 80 | 3.0 |
| Microcrystalline wax | 1.0 |
| lanolin alcohol | 1.0 |
| Carbopol 940 | 0.5 |
| BHA and BHT | 0.02 |
| methyl and propyl paraben | 0.005 |
| Water | To make 100% by weight |

Example 2

| | |
|---|---|
| UFA | 10.0 |
| oleic acid | 10.0 |
| stearic acid | 5.0 |
| palmitic acid | 2.0 |
| triethanolamine | 1.0 |
| TWEEN 60 | 1.5 |
| linoleic acid | 1.0 |
| cetylic acid | 1.0 |
| BHA and BHT | 0.02 |
| methyl and propyl paraben | 0.005 |
| Water | To make 100% by weight |

Example 3

| | |
|---|---|
| magnesium lanolate | 12.0 |
| UFA | 12.0 |
| jojoba oil | 10.0 |
| oleic acid | 6.0 |
| Mineral Oil | 4.0 |
| propylene glycol | 3.0 |
| BHA and BHT | 0.01 |
| methyl and propyl paraben | 0.005 |
| Water | To make 100% by weight |

Example 4

| | |
|---|---|
| UFA | 8.0 |

| | |
|---|---|
| Mineral Oil | 5.0 |
| jojoba oil | 5.0 |
| Glycerol stearate | 3.0 |
| magnesium lanolate | 2.0 |
| propylene glycol | 1.0 |
| BHA and BHT | 0.01 |
| methyl and propyl paraben | 0.005 |
| Water | To make 100% by weight |

In addition, it has been found that the addition of certain metal chelates appears to significantly augment or potentiate the UFA effect on damaged skin. It is not yet certain why or how these ingredients contribute to the positive effects of UFA. The effect is a repeatable improvement in the speed and the extent of UFA amelioration of stretch marks, keratoses, or other skin damage as measured in the above-described and similar studies.

The metal chelates used are either or both zinc and copper CHELAZOME amino acid chelate produced by Albion Laboratories of Clearfield, Utah. Both copper and zinc are known to be cofactors for dermal wound healing. It is not presently known to what extent other types of metal chelates are efficacious. The chelates are primarily soluble in water with the zinc chelate being soluble to about 3.5% by weight and the copper chelate being soluble to about 22% by weight. The chelates are introduced into the cream by being included in the water phase at between about 0.05 to 2.0% by weight of either or both chelates.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for treating skin keratoses or striae distensae, the method comprising topically applying, to an affected area of skin, a dermatologically acceptable composition comprising a concentration of between 5 and 15 weight percent of unsaponifiable lipids from avocado fruit or seed.

2. The method of claim 1, wherein the dermatologically acceptable composition is an emulsion between the lipids and an aqueous phase.

3. The method of claim 2, wherein the emulsion also contains effective concentrations of metal chelates.

4. The method of claim 3, wherein the metal chelates are selected from the group consisting of zinc amino acid chelate, copper amino acid chelate and both zinc and copper amino acid chelates.

5. The method of claim 4, wherein the effective concentration of the selected metal chelates is between about 0.1 and 2.0 weight percent of each metal chelate.

6. A dermatologically acceptable composition for the treatment of skin keratoses or striae distensae, the composition being an emulsion comprising:
a fatty phase comprising:
dermatologically acceptable fats, oils and waxes;
a concentration of between 6 and 15 weight percent of unsaponifiable lipids from avocado seed or fruit; and
a water phase comprising a mixture of water, preservatives and emulsifiers.

7. The composition of claim 6, further comprising an effective concentration of metal chelates selected from the group consisting of zinc amino acid chelate, copper amino acid chelate and both zinc and copper amino acid chelates.

8. The composition of claim 6, wherein the concentration of the selected metal chelates is between 0.1 and 2.0 weight percent of each metal chelate.

9. A dermatologically acceptable composition for the treatment of skin keratoses or striae distensae, the composition being an emulsion comprising:
a fatty phase of between about 25 and 75 weight percent, the fatty phase comprising:
dermatologically acceptable fats, oils and waxes; and
unsaponifiable avocado lipids making up between 5 and 15 weight percent of the emulsion; and
an aqueous phase comprising:
a mixture of water, preservatives and emulsifiers; and
metal chelates selected from the group consisting of zinc amino acid chelate, copper amino acid chelate and zinc and copper amino acid chelates, wherein the concentration of each selected metal chelate is between about 0.1 and 2.0 weight percent.

10. A method for treating skin keratoses or striae distensae comprising repeatedly applying topically, to an affected area of skin, a dermatologically acceptable emulsion of oil and water comprising between 5 and 15 weight percent unsaponifiable avocado seed lipids and metal chelates selected from the group consisting of zinc amino acid chelate and copper amino acid chelate.

11. The method of claim 10, wherein each selected metal chelate is present at a concentration between about 0.1 and 2.0 weight percent.

12. A method for treating skin keratoses or striae distensae, the method comprising topically applying, to an affected area of skin, a dermatologically acceptable composition, the composition comprising:
a concentration of between 5 and 15 weight percent of unsaponifiable lipids from avocado fruit or seed; and
an effective concentration of metal chelates selected from the group consisting of zinc amino acid chelate, copper amino acid chelate and both zinc and copper amino acid chelates, wherein the effective concentration of the selected chelates is between about 0.1 and 2.0 weight percent of each metal chelate.

13. A dermatological composition, the composition being an emulsion comprising:
a fatty phase comprising:
dematologically acceptable fats, oils and waxes;
a concentration of between 5 and 15 weight percent of unsaponifiable lipids from avocado seed or fruit;
an effective concentration of metal chelates selected from the group consisting of zinc amino acid chelate, copper amino acid chelate and both zinc and copper amino acid chelates; and
a water phase comprising a mixture of water, preservatives and emulsifiers.

* * * * *